United States Patent [19]

Brown et al.

[11] Patent Number: 4,566,876

[45] Date of Patent: Jan. 28, 1986

[54] META-PHENYLENEDIAMINE COUPLER COMPOUNDS AND OXIDATIVE HAIR DYE COMPOSITIONS AND METHODS USING SAME

[75] Inventors: Keith C. Brown, New Canaan; John F. Corbett, Norwalk, both of Conn.

[73] Assignee: Clairol Incorporated, New York, N.Y.

[21] Appl. No.: 474,110

[22] Filed: Mar. 10, 1983

[51] Int. Cl.[4] .......................... C07C 91/42; A61K 7/13
[52] U.S. Cl. ........................................... 8/411; 8/429; 564/443; 564/430
[58] Field of Search ................ 564/443, 442, 430; 8/411, 429

[56] References Cited

U.S. PATENT DOCUMENTS

| | | | |
|---|---|---|---|
| 1,935,554 | 4/1931 | Grether et al. | 564/442 |
| 3,037,057 | 5/1962 | Tinsley et al. | 564/442 |
| 3,666,812 | 5/1972 | Kalopissis et al. | 564/443 |
| 3,849,503 | 11/1974 | Shigehara et al. | 568/586 |
| 4,125,367 | 11/1978 | Bugaut et al. | 8/411 |
| 4,330,292 | 5/1982 | Bugaut et al. | 8/411 |

*Primary Examiner*—Charles F. Warren
*Assistant Examiner*—John A. Sopp
*Attorney, Agent, or Firm*—Gabriel P. Katona

[57] ABSTRACT

2-Equivalent oxidative hair dye coupler compounds of the formula (I)

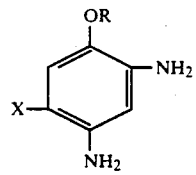

wherein X is halogen or OR', wherein R and R' may be the same or different and represent alkyl, mono- or poly-hydroxyalkyl, alkoxyalkyl, alkylphenyl, aminoalkyl, mono- and di-alkylaminoalkyl, phenyl or phenylalkyl except that R and R' are not both methyl, and the acid addition salts thereof are used in oxidative hair dye compositions with conventional para bases. The amount of oxidizing agent can be reduced relative to similar compositions containing 4-equivalent meta coupler compounds. Some of the compounds of formula (I) in which X is OR' are novel compounds as is the elimination of HOR' during the oxidative coupling reaction.

14 Claims, No Drawings

META-PHENYLENEDIAMINE COUPLER COMPOUNDS AND OXIDATIVE HAIR DYE COMPOSITIONS AND METHODS USING SAME

BACKGROUND OF THE INVENTION

This invention relates to 2-equivalent coupler compounds for oxidative hair dye compositions, some of which are also novel compounds, 1,5-disubstituted-2,4-dinitrobenzene intermediary compounds thereof, as well as to oxidative hair dyeing compositions and hair dyeing methods using these coupler compounds. More particularly, this invention relates to a class of 2-equivalent oxidative hair dye coupler compounds which are meta-phenylenediamines with additional substituents at the 1-position and at the 5-position of the benzene ring. During the oxidative coupling reaction between the oxidative dye coupler and an oxidation developer or base, the 5-substituent is eliminated.

Oxidative dye couplers based on meta-disubstituted benzene compounds, such as meta-phenylenediamine and aminophenol compounds are well known and are highly desirable for their ability to form substantive and strongly colored hair dyes in various colors upon reaction with suitable oxidation developers.

One of the earliest known successful meta-phenylenediamine coupler compounds was meta-diaminoanisol disclosed by Erlenbach in U.S. Pat. No. 992,947. In U.S. Pat. No. 1,144,181, Erhlenbach and Marks disclosed that additional stability to these coupler compounds is provided by using them in the form of their salts, such as the hydrochloride salt.

Nevertheless, the art has actively sought for new oxidative dye couplers are dermatologically and toxicologically innocuous and which possess other properties required for hair dye compositions, such as color intensity and fastness, stability, absorbability to the hair and the like.

U.S. Pat. No. 1,940,757 to Lehmann, et al discloses derivatives of phenylalkylsulfides of the formula

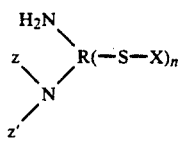

in which R represents phenyl, halogenophenyl, alkylphenyl, hydroxyphenyl or alkoxyphenyl, X represents alkyl or hydroxyalkyl, z and z' represent hydrogen, alkyl or hydroxyalkyl and n is 1 or 2.

Seemuller, in U.S. Pat. No. 3,184,387, discloses polyaminophenols of the formula

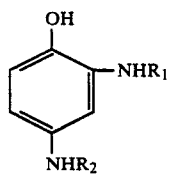

and, in U.S. Pat. No. 3,134,721, polyaminophenols of the formula

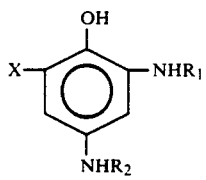

wherein $R_1$ and $R_2$ each represent a hydrogen atom, a lower alkyl group or a lower hydroxyalkyl group with the proviso that at least one of them represents a hydrogen atom and X represents halogen, amine, hydroxyl, carboxyl, lower alkyl, lower alkoxy or nitro.

More recently, meta-phenylenediamine oxidative hair dye couplers of the formula

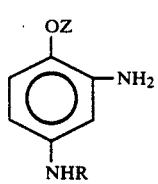

wherein R is either hydrogen, $C_1$–$C_3$ alkyl or $C_1$–$C_3$ hydroxyalkyl and Z represents hydroxyalkyl, alkoxyalkyl, mesylaminoalkyl, acetylaminoalkyl, ureidoalkyl or carbethoxyaminoalkyl, except that Z is not hydroxyethyl when R is hydrogen, are disclosed by Bugaut, et al in U.S. Pat. Nos. 4,125,367 and 4,259,261.

Other aminophenol and meta-phenylenediamine oxidative hair dye couplers are disclosed in U.S. Pat. Nos. 3,546,293—Kalopissis, et al, 3,558,259—Kalopissis, et al, 3,811,831—Bugaut, et al, 4,171,203—Rose, et al, and 4,323,360—Bugaut.

U.S. Pat. No. 3,005,143 to Bohm, et al relates generally to a method for manufacturing aromatic diamines having an alkyl or alkoxy substituent with up to 6 carbon atoms. The product compounds are described as intermediate products for the manufacture of dyestuffs and diisocyanates.

In U.S. Pat. No. 1,919,580 to Wagner, et al, compounds of the formula

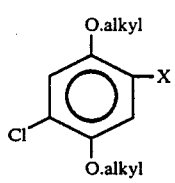

wherein X represents hydrogen, nitro, or amino, are disclosed as compounds having yellow coloration.

U.S. Pat. No. 2,056,299 to Sexton discloses hydroquinone di($\beta$-alkoxyethyl)-ethers and amino and acylamino derivatives thereof which are useful in the manufacture of azo dyestuffs.

Compounds of the formula

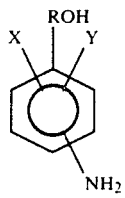

wherein R may be a $C_2$–$C_6$ alkylene or oxyalkylene group and X and Y may each be, independently of the other, hydrogen, halogen, $C_1$–$C_4$ alkyl or alkoxy and amino ($NH_2$) are known from Tinsley, et al U.S. Pat. No. 3,037,057. These compounds are disclosed as dye intermediates, particularly cellulose alkylcarboxylate esters, as well as for their utility as cross-linking or hardening agents for various resin compositions, particularly, epoxy resins.

A discussion of 2-equivalent and 4-equivalent couplers for benzoquinone imines is provided by John F. Corbett at J. Chem. Soc. Vol. Perkin II, 1972, pp. 999–1005. The reaction mechanism, and kinetics of the reaction, between 2,4-diamino-1,5-dimethoxy-benzene (4,6-dimethoxy-m-phenylenediamine) and benzoquinone mono-imine or benzoquinone di-imine are studied and the author concludes that in these reactions 2,4-diamino-1,5-dimethoxybenzene behaves as a 2-equivalent coupler in which a methoxy group is displaced. No practical application of this reaction is described, however. Furthermore, as will be shown hereinafter, the dimethoxy m-phenylenediamine compound does not produce a colorfast hair dye composition.

Accordingly, there is still a need in the art for further improvements in oxidative couplers for hair dyeing compositions, especially for compounds which undergo rapid reaction with the oxidation developer without requiring excessive amounts of oxidizing agents, such as hydrogen peroxide, and which have improved colorfastness.

SUMMARY OF THE INVENTION

It has now been found that the class of compounds having the following formula (I)

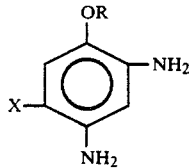 (I)

wherein R represents alkyl, hydroxyalkyl, polyhydroxyalkyl, alkoxyalkyl, alkylphenyl, aminoalkyl, mono- and di-alkyl aminoalkyl, phenyl or phenylalkyl, and X represents a halogen atom or the group —OR' where R' has the same meaning as R and when X is —OR', the groups —OR and —OR' may be the same or different except that R and R' may not both be methyl at the same time; and the acid addition salts thereof, are 2-equivalent oxidative dye couplers which are safe and effective components of hair dyeing compositions and which, depending on the selection of the oxidation developer, can yield long-lasting blue, blue-violet, or brown dyes which are substantive to keratinic fibers, especially human hair. When the oxidative dye coupler compounds of formula (I) are contacted with an oxidation developer in the presence of an oxidizing compound such as hydrogen peroxide, a color forming coupling reaction takes place in which the halogen or OR' substituent at the 5-position is eliminated in the form of the corresponding haloacid or HOR' and only two equivalents of the oxidant are required for conversion into the dye.

The compounds of formula (I) can be prepared by reacting 1,5-dihalo-2,4-dinitrobenzene with at least one compound of formula (III)

MOZ    (III)

wherein M represents an alkali metal or alkaline earth metal and Z has the same definition as R and R' in formula (I) to form a compound of formula (IV):

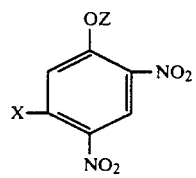 (IV)

wherein X has the same definition as in formula (I). The compound of formula (IV) is then hydrogenated to form the corresponding diamino compound of formula (I).

Some of the compounds of formulas (I) and (IV) in which X is OR' are novel compounds. The elimination of R'OH from the oxidative coupler compound of formula (I) during the coupling reaction with the oxidation developer is also believed to be a novel reaction in hair dyeing compositions.

Accordingly, in one aspect the present invention provides novel compounds of formula (I-a)

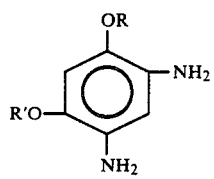 (I-a)

wherein R and R' may be the same or different and have the same definitions as given above except that R and R' are not both methyl and when R is hydroxyalkyl, R' is not alkyl; and the acid addition salts thereof.

The present invention also provides the novel compounds of formula (IV-a)

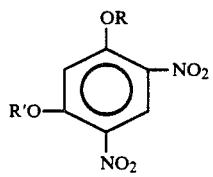 (IV-a)

wherein R and R', which may be the same or different, have the same definitions as given above with regard to formula (I-a).

In another aspect, the present invention provides a process for preparing the disubstituted dinitrobenzene compounds of formula (IV-a) in which 1,5-dihalo-2,4-dinitrobenzene is reacted with at least one organic salt compound of formula (III) to form a compound of formula (IV-a).

The present invention also provides a process for preparing the 2-equivalent coupler compounds of formula (I), the process involving the hydrogenation of the disubstituted dinitrobenzene compound of formula (IV).

In a specific embodiment of this aspect of the invention, the compounds of the formula (I-a) are prepared by reacting 1,5-dihalo-2,4-dinitrobenzene with a mixture of an organic salt of formula (III-1)

MOR      (III-1)

and an organic salt of formula (III-2)

MOR'     (III-2)

wherein M, R and R' are as defined above and R and R' may be the same or different to produce a compound of formula (IV-a)

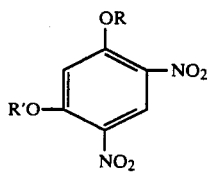    (IV-a)

and hydrogenating the compound of formula (IV-a) to produce the novel 2-equivalent meta-phenylenediamine coupler compound of formula (I-a):

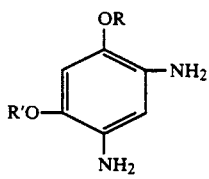    (I-a)

In addition to providing the novel compounds of formula (I-a) and (IV-a), the present invention also provides aqueous oxidative hair dye compositions, which are based on a mixture of at least one oxidative dye coupler compound of formula (I) and at least one oxidative developer compound capable of forming a dye upon reaction with the oxidative dye coupler compound which is substantive to keratinic fiber, especially human hair.

The present invention, in another aspect, provides a two compartment hair dyeing package wherein in the first compartment a hair dyeing composition comprising a predetermined amount of a hair dyeing composition which comprises a mixture of at least one oxidative 2-equivalent coupler compound of formula (I) and at least one oxidative developer compound capable of forming a dye upon reaction with the oxidative dye coupler compound which is substantive to human hair is provided and in the second compartment a stabilized peroxide oxidizing agent is provided in an amount sufficient to oxidize all of the oxidizable components of the hair dyeing composition in the first compartment; wherein the contents of the two compartments are isolated from each other and may be combined just prior to application to the hair.

In still another aspect of the present invention, a method is provided for dyeing keratinic fibers, particularly human hair by applying to the keratinic fiber or human hair a mixture of at least one oxidative dye coupler compound of formula (I) and at least one oxidation developer compound which can react with the coupler compound(s) to form a keratinic fiber- and human hair-substantive dyestuff in the presence of an oxidizing agent.

DETAILED DESCRIPTION OF THE INVENTION AND PREFERRED EMBODIMENTS

The oxidation dye couplers of this invention are designated as 2-equivalent couplers: they bear a suitable leaving group X at the 5-position (para to an amino group substituent) which give leuco-bases which are converted into the dye, e.g. indamine dyes, by elimination of HX. This dye forming reaction using the 2-equivalent couplers of this invention can be represented by the following series of reactions:

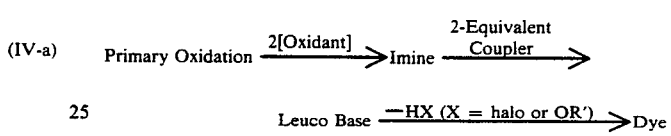

In contrast, with conventional 4-equivalent dye couplers such as exemplified in the above mentioned patents, the leuco base is converted into the dye by elimination of two hydrogen atoms requiring two additional equivalents of oxidant. It is noted, however, that in both cases, the final dye product will be the same.

In the present invention, the leaving group X may be halogen or the group OR', i.e. the dye-forming coupling reaction between the oxidative dye coupler and oxidation developer eliminates HX, for example, HCl, HOCH$_2$CH$_2$OH, HOCH$_3$, etc.

The oxidative dye couplers of this invention are compounds of formula (I):

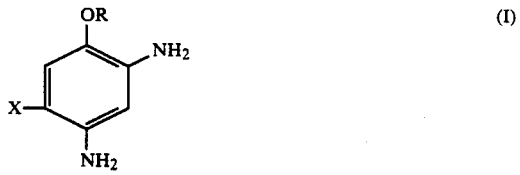    (I)

wherein R represents alkyl, hydroxyalkyl, polyhydroxyalkyl, alkoxyalkyl, alkylphenyl, aminoalkyl, mono- and di-alkylaminoalkyl, phenyl or phenylalkyl, and X represents a halogen atom or the group —OR' where R' has the same meaning as R and when X is —OR', the groups —OR and —OR' may be the same or different; and the acid addition salts thereof.

In the 1,5-disubstituted m-phenylenediamine compounds described above in Formula I the chain length of the alkyl chain or alkyl moiety of the compound radicals (e.g. hydroxyalkyl, phenylalkyl) may vary. Ordinarily, the alkyl chain or alkyl moiety will be of the lower chain length variety containing 1 to 6 carbon atoms, especially 1 to 4 carbon atoms. When R' is a hydroxyalkyl radical it will ordinarily contain from 1 to 3 hydroxy groups.

To further illustrate more specifically the various values that R and R' may have in Formula I, the following are given:

(1) R=alkyl: methyl, ethyl, n-propyl, isopropyl, n-butyl, isobutyl, tert-butyl, pentyl, hexyl;

(2) R=hydroxyalkyl: (preferably 2 to 6 carbon atoms and 1 to 3 hydroxy groups); hydroxymethyl, 2-hydroxyethyl, 3-hydroxypropyl; 2,3-dihydroxypropyl, 4-hydroxybutyl; 1,3-dihydroxypropyl, 4-hydroxybutyl; 1,3-dihydroxypropyl, tris(hydroxymethyl)-methyl;

(3) R=alkoxyalkyl: methoxymethyl, methoxyethyl, ethoxymethyl, ethoxyethyl, propoxymethyl, propoxyethyl, butoxyethyl, etc., preferably those having a total of 2 to 5 carbon atoms in the alkoxy and alkyl moieties;

(4) R=alkylphenyl: benzyl, phenylethyl, phenylpropyl,

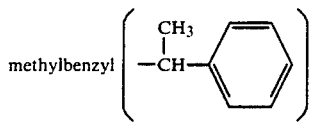

methylbenzyl

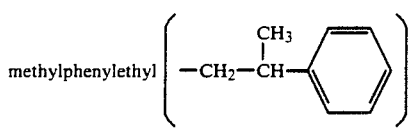

methylphenylethyl (5) R=aminoalkyl: methylamino (—CH$_2$NH$_2$), ethylamino, n-propylamino, isopropylamino, n-butylamino;

(6) R=mono- or di-alkylaminoalkyl: (—R$_1$NR$_2$R$_3$ where R$_1$ is alkyl, preferably C$_1$-C$_3$, and R$_2$ and R$_3$ are independently, hydrogen or alkyl, preferably C$_1$-C$_3$, with the proviso that at least one of R$_2$ and R$_3$ is alkyl); e.g. methylaminomethyl, methylaminoethyl, ethylaminoethyl, ethylaminoethyl, N-methyl, N-ethylaminomethyl, N,N-diethylaminoethyl, N,N-diethylaminorpopyl, etc.;

(7) R=phenyl: phenyl

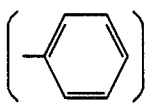

(8) R=phenylalkyl: phenylmethyl

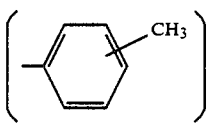

phenylethyl

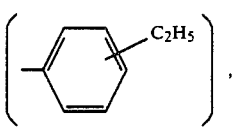

etc.

When X is a halogen atom it may be Cl, Br or I, preferably Cl or Br, especially preferably Cl, although when the compositions are to be applied to keratinic fibers other than living human hair, other halogen atoms, for example, fluorine, may also be used.

Among the above groups of compounds of formula (I) it has been found that the best results are obtained with those compounds in which X represents OR' and R and R' are alkyl or hydroxyalkyl with the total number of carbon atoms in R and R' being at least 3, preferably from to carbon atoms. These, accordingly, form a preferred group of meta coupler components which can be advantageously used in oxidation dye compositions in accordance with the present invention.

Of this preferred group of meta couplers the compounds of formula (I-a) are novel compounds:

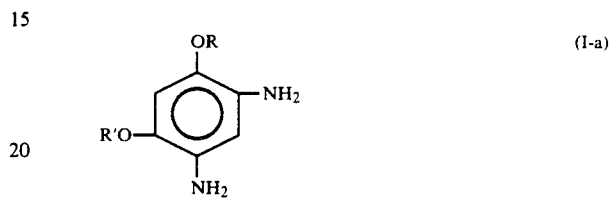

wherein R represents alkyl, hydroxyalkyl, polyhydroxyalkyl, alkylphenyl, aminoalkyl, mono- or dialkylaminoalkyl, phenyl or phenylalkyl, and R' may be the same or different as R except that when R represent methyl, R' does not also represent methyl, and when R represents hydroxyalkyl, R' does not represent alkyl.

The compound of formula (I) in which X is OR' and R=R'=CH$_3$ is 4,6-dimethoxy-m-phenylenediamine which has been disclosed in the above-mentioned article by J. F. Corbett to be a 2-equivalent coupler in the coupling reaction with benzoquinone imines.

Surprisingly, it has now been found that in the coupling reaction with p-phenylenediamine color developers used in hair dye compositions the colorfastness of the dialkoxy m-phenylenediamine compounds of formula (I-a) wherein R and R' are both alkyl with the total number of carbon atoms in the two alkoxy groups being 3 or more are unexpectedly superior to the colorfastness of the compound disclosed by Corbett, i.e. R=R'=CH$_3$ (a total of 2 carbon atoms in the dimethoxy groups).

The compounds of formula (I) in which R is hydroxyalkyl and X is halogen or X is OR' and R' is alkyl, i.e. compounds of formula

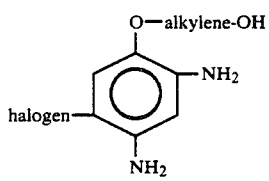

and

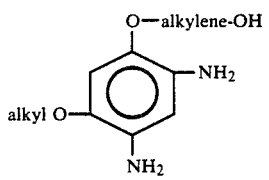

are generically disclosed in the aforementioned U.S. Pat. No. 3,037,057 to Tinsley, although the properties of these compounds as 2-equivalent couplers for hair dye compositions is not at all suggested in this patent.

The coupler compounds of this invention can be readily prepared by the following reactions which, individually, are generally well-known in the art. Thus, the compounds of formula (I) in which X is the OR' group, i.e. compounds of formula (I-a), in which R and R' are hydroxyalkyl, are prepared by reacting 1,5-halo-2,4-dinitrobenzene, e.g. 1,5-dichloro-2,4-dinitrobenzene, with the corresponding glycol salt or salts in an appropriate glycol solvent. When the groups OR and OR' are the same, a slight molar excess (about 2 to 3 moles) of an alkali metal alkylene glycollate is added to an alkylene glycol solvent solution containing about 1 mole of 1,5-dichloro-2,4-dinitrobenzene and the mixture is slowly heated until the product 4,6-dinitroresorcinol-bis(2-hydroxyalkyl) ether of formula (IV-a) is obtained. This product is then hydrogenated to convert the nitro groups to amine groups to obtain the product 4,6-diaminoresorcinol-bis(2-hydroxyalkyl) ether. Where the OR and OR' groups are not the same, the mixed ethers can be prepared by consecutive addition of two different alkali metal alkylene glycollates, or by reaction of the chloromonoether with a different alkali metal alkylene glycollate.

When one or both of R and R' are other than hydroxyalkyl generally the same scheme can be used by substituting the corresponding salt MOR or MOR', where M may be an alkali metal or other suitable cation, for the alkali metal alkylene glycollate, to produce the corresponding disubstituted dinitrobenzene compound of formula (IV-a) which is then hydrogenated to the m-phenylenediamine compound of formula (I-a).

To prepare the compounds of formula (I) wherein X is halogen, the same procedure as described above can be used except that the molar ratio of 1,5-dihalo-2,4-dinitrobenzene to the alkali metal alkylene glycollate or other MOR salt, as the case may be, will be about 1:1 to about 1:1.5. The reaction can be monitored, for example, by chromatographic methods, to detect the formation of the mono-substituted dinitro-monochlorether. The process disclosed in U.S. Pat. No. 3,037,057 can also be used.

The hydrogenation reaction can be carried out according to conventional procedures by contacting the dinitrobenzene compound of formula (IV) with hydrogen gas in the presence of a hydrogenation catalyst, preferably a noble metal catalyst. For example, suitable conditions for the catalytic hydrogenation reaction are disclosed in U.S. Pat. No. 4,005,143.

The oxidative dye coupler compounds of formula (I) according to the invention can be used as such or preferably in the form of their salts with inorganic or organic acids. Useful salts include, for example, chlorides, sulfates, phosphates, acetates, propionates, lactates, citrates, and the like.

The dyes described above in formulas (I) and (I-a) are intended for use mainly as meta coupler components in oxidation dye compositions. These are usually aqueous alkaline compositions that contain, in addition to the meta component (coupler) at least one para component (developer or base). Optionally, such composition may also contain such things as modifier dye intermediates, nitro dyes, soaps, surfactants, thickening agents, antioxidants and organic solvents. Furthermore, these aqueous compositions may take various forms such as solutions, flowable liquids, pastes, creams or gels.

As illustrative of the para components that may be used as the oxidation dye developer in this invention mention may be made of the following: p-toluenediamine, p-aminophenol, p-aminodiphenylamine, 4,4'-diaminodiphenylamine, 2,6-dimethyl-p-phenylenediamine, 2,5-diaminopyridine. The class of para components described in the following formula (II):

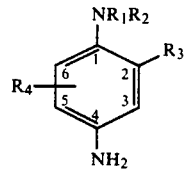

(II)

or its non-toxic salts, in which:
$R_1$ is hydrogen, alkyl or hydroxyalkyl;
$R_2$ is hydrogen or hydroxyalkyl;
$R_3$ is hydrogen, alkyl, alkoxy or halogen; and
$R_4$ occupies any one of the remaining positions on the benzene radical and is hydrogen, alkyl, alkoxy or halogen; are of particular value. Para components of formula II in which $R_2$ is hydrogen when $R_3$ is alkyl, alkoxy or halogen and providing that at least two of $R_1$, $R_2$, $R_3$ or $R_4$ are other than hydrogen, are of special interest. In this case too, the alkyl groups or alkyl moieties contain 1 to 5 carbon atoms and the hydroxyalkyl contains from 1 to 3 hydroxy groups. The halogen may be Cl, Br, F, I, etc., preferably, Cl or Br. p-Phenylenediamine is especially preferred.

In addition to the meta and para components, the oxidation dye compositions of this invention may contain other modifier dye intermediates. These include such things as the m-aminophenols, compounds containing active methylene groups, phenols, etc. Meta-aminophenols can give either indophenols or indamines on oxidative coupling with para components. The products are usually violet in color and are used in modifying shades. Examples of aminophenols useful herein are 2,4-diaminophenol, m-aminophenol, aminoresorcinol, 1,5-aminohydroxynaphthalene and 1,8-aminohydroxynaphthalene.

Compounds containing active methylene groups are also capable of reacting with the oxidatively activiated para components. The products are imino compounds of various types and are yellow or red in color. Examples of active methylene compounds employable in the present invention includes for example, 3-methylpyrazolone-(5), 1-phenyl-3-methylpyrazolone-(5); 1,3-dimethylpyrazolone-(5), acetoacetic acid anilide, benzoylacetotoluide and nicotinoylacetanilide.

Still other oxidation dye intermediates, i.e. modifiers, may be present in the compositions of this invention which produce colored products under oxidative conditions by more complex mechanisms. These may include one or more of self-coupling, or coupling with the para components or with other intermediates present. Among these may be mentioned hydroquinone, catechol, 1,5-naphthalenediol, o-phenylenediamine, o-aminophenol.

Phenols react with para components, in the presence of oxidizing agents, to produce indophenols. These are usually blue or violet compounds, although resorcinols give yellow or brown colored compounds under these conditions. The brown colors obtained from the reaction of resorcinols are commonly used to produce the depth of a shade. Examples of phenols useful in oxidation dye compositions of this invention are pyrogallol, resorcinol, pyrocatechol and alphanaphthol.

It is sometimes desirable to add to the oxidation dye mixtures dyes which are already colored, i.e. which do not require an oxidizing agent for color development. These are generally added for blending purposes to obtain natural looking colors in the final dyeing operation. One class of dyes which may be used for this purpose is the nitro dyes and this component is generally referred to herein as the nitro dye components. A large number of nitro dyes are known in the art which are suitable for this purpose. The only limitation that is placed on a nitro dye to be useful in the present invention is that it be one whose color is not destroyed by the oxidizing agent used in the final color development of the oxidizable components. By way of illustration of suitable nitro dyes, mentioned may be made of the following: 4-nitro-o-phenylenediamine, 2-nitro-p-phenylenediamine, 4-nitro-2-aminophenol, 5-nitro-2-aminophenol, 2-nitro-4-aminophenol and picramic acid.

The pH of the oxidation dye mixture of this invention will generally be on the basic side e.g. 8–11. It is preferred, however, that this pH be in the range of about 9–10.

Any of a wide variety of alkalizing agents can be used to adjust the pH of the dyeing composition on the basic side. Ammonium hydroxide, because of its freedom from toxicity over a wide concentration range and its economy, is an acceptable alkalizing agent. However, there can be used in place of, or together with, ammonia any other compatible ammonia derivative as an alkalizing agent, such as an alkylamine, such as ethylamine, or triethylamine; or alkanolamine, such as monoethanolamine or diethanolamine. Likewise, any other of the common alkalizing agents may be used, such as sodium or potassium hydroxide, sodium or potassium carbonate, sodium phosphate, sodium hydrogen phosphate, sodium silicate, and the like.

Among the soaps which may be present in the compositions of this invention there may be mentioned the sodium, ammonium or potassium salts of lauric, stearic, palmitic, oleic, linoleic or ricinoleic acid. The soaps may be present to the extent of 5–35% of the weight of the oxidation dye mixture, and preferably 15–25%.

Among the surface active agents useful in the present invention, mention may be made of the water-soluble surface active agents. These can be anionic, non-ionic or cationic. Illustrative of the various types of water-soluble surface active agents there can be mentioned: higher alkylbenzenesulfonates, alkylnaphthalenesulfonates; sulfonated esters of alcohols and the polybasic acids; taurates; fatty alcohol sulfates; sulfates of branched chain or secondary alcohols; alkyl dimethylbenzyl ammonium chlorides; and the like. Illustrative of specific surfactants there can be mentioned: sodium lauryl sulfate; polyoxyethylene lauryl ester; myristyl sulfate; glyeryl monostearate; sodium salt of palmitic methyl taurine; cetyl pyridinium chloride; lauric diethanolamide; polyoxyethylene stearate; stearly dimethyl benzyl ammonium chloride; dodecyl benzene sodium sulfonate; nonyl naphthalene sodium sulfonate; dioctyl sodium sulfosuccinate; sodium N-methyl-N-oleoyl taurate; oleic acid ester of sodium isothionate; sodium dodecyl sulfate; the sodium salt of 3,9-diethyl-tridecanol-6-sulfate and the like. The quantity of water-soluble surface active agent when present can vary over a wide range, such as that of from about 0.5% to 30% by weight of the composition, and preferably 1–10%.

Various organic solvents may also be present in the oxidation dye mixture for the purpose of solubilizing a dye intermediate or any other component which may be insufficiently soluble in water. Generally, the solvent selected is such as to be miscible with water and innocuous to the skin and includes for example, ethanol, isopropanol, glycerine, ethylene glycol, propylene glycol, ethylene glycol monoethyl ether, diethylene glycol, diethylene glycol monoethyl ether, etc. The amount of solvent used may vary from 1–40% of the oxidation dye mixture and preferably 5–30%.

To exemplify the thickening agents that can also be incorporated in the present dyeing composition, mention may be made of sodium alginate or gum arabic or cellulose derivatives such as methylcellulose, hydroxyethylcellulose, or the sodium salt of carboxymethylcellulose, or acrylic polymers, such as polyacrylic acid sodium salt, or inorganic thickeners, such as bentonite. The quantity of thickening agent when present can vary over a wide range, such as that of from about 0.5% to 5% and preferably from about 0.5% to 3% by weight.

To illustrate the antioxidants that may be used in the present oxidation dye mixture, mention may be made of sodium sulfate, thioglycollic acid, sodium hydrosulfite and ascorbic acid. The quantity of antioxidant that may be contained in the instant oxidation dye mixture will usually be in the range of from about 0.05% to 1% by weight based on the total weight of the oxidation dye mixture.

Water is ordinarily the major constituent of the present composition and can vary over a wide range dependent in large measure on the quantity of other additives. Thus, the water content can be as little as 20% and preferably from about 30% to 90%.

The dyeing compositions of this invention are preferably aqueous compositions. The term "aqueous composition" is used herein in its usual generic sense as embracing any water-containing composition embodied in the invention. This includes true solutions or mixtures of the dye in an aqueous medium, either alone or in conjunction with other materials, which are also dissolved or dispersed in the aqueous medium. The dye may be colloidally dispersed in the medium or may merely be intimately mixed therein.

To further illustrate the various other modifiers, antioxidants, alkalizers, thickeners, chelating agents, perfumes and other adjuvants that may be incorporated in the oxidation dye mixture of this invention, reference is made to Sagarin "Cosmetics, Science and Technology" (1957), pages 505–507, Interscience Publishers, Inc., New York. The aqueous compositions of this invention may take many forms. Thus, they may be thin or thick flowable liquids, pastes, creams, gels etc.

To summarize the various components that may comprise the oxidation dye mixture of this invention, Table I below is given. The percentages are given as percent by weight based on the total weight of the oxidation dye mixture.

TABLE 1

| Components | % by weight | |
|---|---|---|
| | General | Preferred |
| Para developer component | 0.01 to 6 | 0.02 to 4 |
| Coupler component (formula I) | 0.01 to 6 | 0.02 to 4 |
| Other oxidation dye intermediate | 0 to 4 | 0.01 to 2 |
| Nitro dyes | 0 to 3 | 0.01 to 2 |
| Soap | 0 to 35 | 10 to 25 |

TABLE 1-continued

| Components | % by weight | |
|---|---|---|
| | General | Preferred |
| Surfactant | 0 to 30 | 1 to 10 |
| Thickening Agent | 0 to 5.0 | 0.05 to 3 |
| Antioxidants | 0 to 1.0 | 0.05 to 1 |
| Organic solvents | 0 to 40 | 5 to 35 |
| Water | QS to 100% | QS to 100% |
| Alkalizing agent to pH | 8 to 11 | 9 to 10 |

The aforesaid oxidation dye mixtures of this invention are intended for use in conjunction with conventional oxidizing agent necessary to effect reaction to colored products. Typical oxidizing agents that are useful for this purpose are aqueous solutions of hydrogen peroxide, e.g. 3 to 12%, or high viscosity creams containing in addition, for example, nonylphenol polyethylene glycol or lauryl alcohol polyethylene glycol, in an amount of from 2–10% of the weight of oxidizer, or crystalline peroxide, such as urea peroxide or melamine peroxide.

In use, a quantity of the oxidizing agent described above is mixed with a quantity of oxidation dye composition described previously. Usually, the amount of oxidizing agent is far in excess of that required to oxidize the intermediates, the amounts taken being dependent on the form and concentration of the oxidizer selected. However, it is one of the important features of the present invention that since the meta coupler component of formula (I), including the novel compounds of formula (I-a), are 2-equivalent couplers and, therefore, only about one-half of the amount of oxidizing agent usually used for oxidation dye compositions, based on 4-equivalent meta couplers, is required to produce the same degree of coloration. Accordingly, the risk of damage to the hair, roots, and scalp due to the excessive amounts of oxidizing agent can be substantially reduced. Or course, to the extent that other oxidation dye intermediates are used in conjunction with the meta coupler compounds of this invention an actual 50% reduction of the total quantity of oxidizing agent may not be practical. Nevertheless, reductions in amount of oxidizing agent up to about 50%, especially up to about 30%, particularly especially from about 5% to 25% can be realized, depending on the meta and para components present in the oxidation dye composition.

In use the mixture is well shaken and applied to hair. It can be applied as a shampoo to the entire head, applied to one area of the hair, such as the roots and combed through the rest of the hair later. The mixture is allowed to remain on the head for a period of time and is then removed by shampooing. The normal time of application is 20–30 minutes, but application times of from 10 minutes to one hour can be used. Room temperature during application is preferred although higher or lower temperatures, e.g. 15°–40° C. can be used.

In one form of application of the compositions of this invention, the oxidation dye mixture is dispensed from an aerosol container under pressure of a suitable propellant. The foam so obtained is mixed with the developer, generally a solution of hydrogen peroxide, and applied to the hair as above.

In a preferred embodiment, the oxidation dye composition, which may be in the form of solution, flowable liquid, paste, cream or gel, is provided in a first container and the stabilized peroxide oxidizing agent is provided separately in a second container, the first and second containers being sold together as a kit for a single application use wherein the contents of the first and second containers are thoroughly mixed together immediately prior to use.

The first and second containers may be individual sealed packages or containers of any suitable material inert to the oxidizing composition and oxidizing agent. Alternatively, the first and second containers may constitute separate but isolated compartments of a single container wherein the first and second compartments are isolated by a seal or diaphragm, for example, which can be removed or punctured to allow the contents to be mixed together in one or theother or both of the compartments. Devices of this nature are well known in the art and have the advantage of providing predetermined dosages of the oxidizing agent and dye composition to achieve the desired color effect.

As used herein and in the appended claims, the terms "compartments" and "containers" are used interchangeably to refer to either of these embodiments, namely, separate unconnected receptacles or packages or separate but isolated receptacles of a single unit package.

The following Examples are given to further illustrate the present invention. It is to be understood, however, that the invention is not limited thereto. Unless otherwise specified, all percentages are given as percent by weight based on the total weight of the composition.

EXAMPLE 1

Preparation of 4,6-bis-[2'-hydroxyethyoxy]-m-phenylenediamine

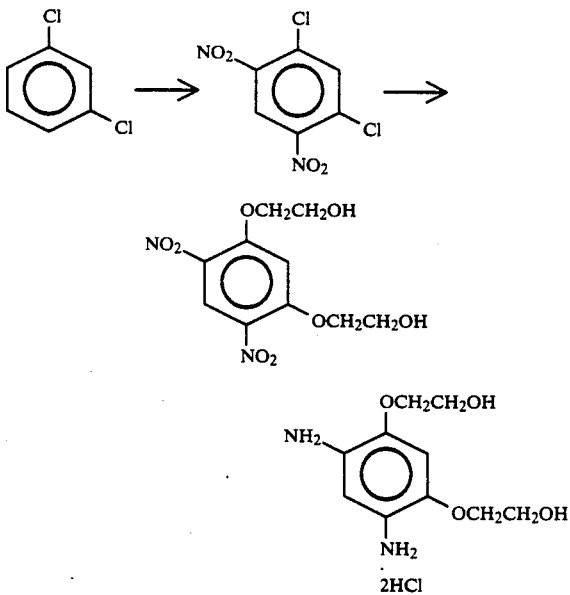

Nitration of m-dichlorobenzene

To a mixture of 800 ml fuming HNO₃ (90%) and 1600 ml conc. H₂SO₄ cooled in an ice bath is added 200 ml [(257.6 g) (1.75 moles)] m-dichlorobenzene over 30 min. After the addition is complete, the ice bath is removed. The temperature of the mildly exothermic reaction rises to approximately 55° C. while still in the ice bath. The ice bath is removed and the mixture is externally heated to 90° C. TLC (hexanes) after about 1 hr. shows no starting material and no mononitro intermediate. The hot mixture is then stirred onto 6 liters of ice. The pale yellow product that precipitates is collected by vacuum filtration and washed of any residual acid with 6 liters water. The product 1,5-dichloro-2,4-dinitrobenzene is recrystallized using absolute ethanol and decolorizing charcoal. Yield of purified material is 291.6 g, m.p. 103° C.

Preparation of 4,6-bis-[2'-hydroxyethoxy]-1,3-dinitrobenzene

To 150.0 g (0.63 moles) 1,5-dichloro-2,4-dinitrobenzene in 1500 ml ethylene glycol is added 159.0 g (1.89 moles) sodium ethylene glycollate over approximately 30 min. The mixture is then slowly heated to 90° C. and the reaction is monitored by TLC (ethyl acetate). TLC after approximately 3 hours shows no starting material and no mono-substituted intermediate. The reaction is shut down and the mixture is allowed to sit at room temperature overnight to crystallize the product. The mixture is then placed in a freezer for about 3 hours to induce further crystallization of the product. The pale yellow product is collected by vacuum filtration and washed free of ethylene glycol with water. The product is dried in a vacuum oven at 50° C. The ethylene glycol/$H_2O$ filtrate is placed in the freezer to yield more product. Yield of Crop #1 is 144.0 g (79.4%). Yield of Crop #2 is 24.5 g (13.5%).

Hydrogenation of 4,6-bis-[2'-hydroxyethoxy]-1,3-dinitrobenzene

Fifty (50.0) grams (0.174 moles) 4,6-bis-[2'-hydroxyethoxy]-1,3-dinitrobenzene in 750 ml absolute ethanol with 2.0 g 5% Pd/C, is reduced on the Parr Hydrogenator at 64° C. $H_2$ uptake is halted after approximately 3 hours at 92% of theoretical uptake. The colorless reaction mixture is dried with molecular sieves while under $N_2$ and is quickly filtered into 2.5 liter ethyl acetate saturated with HCl (g). The white precipitate is quickly collected by vacuum filtration, washed with ethyl acetate, and dried in a vacuum desiccator. Yield is 46.8 g (89.7%).

EXAMPLE 2

Preparation of 4-(2'hydroxyethoxy)-6-chloro-m-phenylenediamine

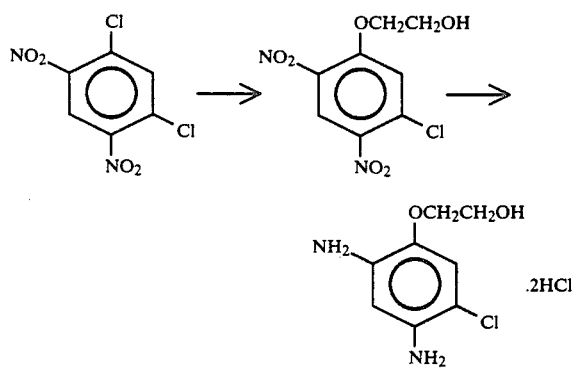

Preparation of 2-(5'-chloro-2',4'-dinitrophenoxy) ethanol 94.8 g (0.40 moles) 1,5-dichloro-2,4-dinitrobenzene in 580 ml ethylene glycol is heated to 50° C. To the mixture is then very gradually added, with stirring, 50.4 g (0.60 moles) sodium ethylene glycoxide over approximately 6 hours. One hour after addition is complete, TLC (ethyl acetate) shows the reaction is complete. The heat is turned off and the mixture is allowed to cool to room temperature. The precipitated product is collected by vacuum filtration and is washed with water. The water causes additional product to precipitate in the filtrate. The product is dried in a vacuum oven at 50° C. Yield of the combined crops is 82.7 g (78.8%), m.p. 98°–100° C.

Hydrogenation of 2-(5'-chloro-2',4'-dinitrophenoxy) ethanol

Then (10.0) grams (0.038 moles) of 2-(5'-chloro-2',4'-dinitrophenoxy) ethanol in 100 ml absolute ehtanol with 400 mg 5% Pd/C is reduced on the Parr Hydrogenator at 65° C. Reaction pressure is 50–55 lbs. $H_2$. Stoichiometric $H_2$ is taken up within 2 hours. The colorless reaction mixture is dried with molecular sieves while under $N_2$ and is quickly filtered into 250 ml ethyl acetate saturated with HCl(g). The white precipitate was quickly collected by vacuum filtration, washed with ethyl acetate, and dried in a vacuum desiccator. Yield of 4-(2'-hydroxyethoxy)-6-chloro-m-phenylenediamine dihydrochloride is 7.0 g (66.7%).

EXAMPLE 3

Preparation of 4,6-dimethoxy-m-phenylenediamine

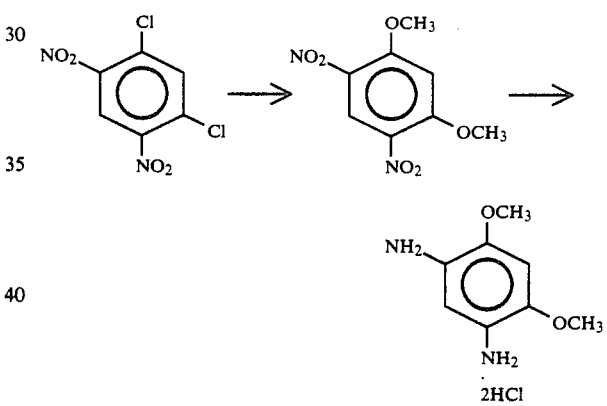

Preparation of 4,6-dimethoxy-1,3-dinitrobenzene

To 20.0 g (0.084 moles) 1,5-dichloro-2,4-dinitrobenzene in 200 ml methanol is added 22.7 g (0.42 moles) sodium methoxide. The mixture is heated to reflux and the reaction is monitored by TLC (ethyl acetate). TLC after approximately 12 hours shows the reaction is complete. The host mixture is poured into 750 ml ice/$H_2O$. The pale yellow precipitate is collected by vacuum filtration and dried in the vacuum oven at 50° C. Yield is 16.3 g (85.7%). Recrystallization using toluene and 1 g decolorizing charcoal yields 11.5 g product, m.p. 153°–155° C.

Hydrogenation of 4,6-dimethoxy-1,3-dinitrobenzene

A mixture of 10.0 g (0.039 moles) of 4,6-methoxy-1,3-dinitrobenzene, 100 ml absolute ethanol and 400 mg 5% Pd/C is equilibrated on the Parr Hydrogenator at 65° C. for one hour. The reaction pressure is set at 50 to 55 lbs $H_2$. When $H_2$ uptake is halted, the mixture is dried with molecular sieves while under $N_2$. This is quickly filtered into 250 ml ethyl acetate through which HCl (g) is bubbled for approximately 5 minutes. The white precipitate is collected by vacuum filtration, washed with ethyl acetate and dried in a vacuum desiccator at room temperature.

EXAMPLE 4

Preparation of
4,6-bis[2',3'-dihydroxypropoxy]-m-phenylenediamine

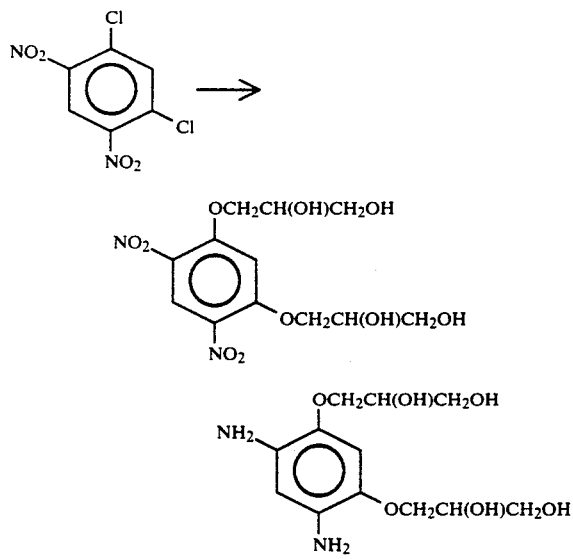

Preparation of
4,6-dinitro-1,3-bis(2',3'-dihydroxypropoxy)-benzene

To 15.0 g (0.063 moles) 1,5-dichloro-2,4-dinitrobenzene in 100 ml glycerol is added 17.3 g (0.15 moles) sodium glyceroxide. The mixture is heated to 65° C. The reaction is monitored by TLC (ethyl acetate). When TLC shows the reaction is complete, the hot mixture is poured onto 1.5 liters ice. The precipitated product is collected by vacuum filtration and dried.

Hydrogenation of
4,6-dinitro-1,3-bis(2',3'-dihydroxypropoxy)-benzene

A mixture of 10.0 g of 4.6-dinitro-1,3-bis(2',3'-dihydroxypropoxy) benzene, 100 ml absolute ethanol, and 400 mg 5% Pd/C is equilibrated on the Parr Hydrogenator at 65° C. for one hour. The reaction pressure is set at 50 to 55 lbs $H_2$. When $H_2$ uptake is halted, the mixture is dried with molecular sieves while under $N_2$. This is quickly filtered into 250 ml ethyl acetate through which HCl (g) is bubbled for about 5 minutes. The white precipitate is collected by vacuum filtration, washed with ethyl acetate, and dried in a vacuum desiccator at room temperature.

EXAMPLE 5

Preparation of
4-(2'-hydroxyethoxy)-6-methoxy-m-phenylenediamine

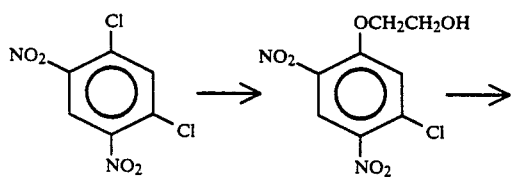

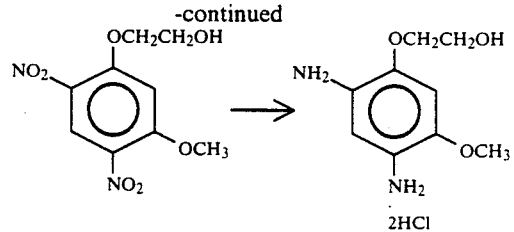

Preparation of 2-(2',4'-dinitro-5'-methoxyphenoxy) ethanol

To 20.0 g (0.076 moles) of 2-(5'-chloro-2',4'-dinitrophenoxy) ethanol in 200 ml methanol is added 10.8 g (0.20 moles) sodium methoxide, with stirring. The mixture is heated to reflux. TLC (ethyl acetate) after 6 hours shows the reaction is complete. The hot mixture is poured into 1 liter ice. The pale yellow precipitate is collected by vacuum filtration, washed with water and dried in a vacuum oven at 50° C. Yield is 16.3 g (82.9%), m.p. 137°–140°.

Hydrogenation of 2-(2',4'-dinitro-5'-methoxyphenoxy) ethanol

Ten (10.0) grams (0.039 moles) of 2-(2',4'-dinitro-5'-methoxyphenoxy) ethanol, in 100 ml absolute ethanol with 400 mg 5% Pd/C, is reduced on the Parr Hydrogenator at 65° C. Stoichiometric $H_2$ is taken up within 1 hour. The colorless reaction mixture is dried with molecular sieves under $N_2$ and is quickly filtered into 250 ml ethyl acetate, through which HCl (g) is bubbled for 5 minutes. The white precipitate is quickly collected by vacuum filtration, washed with ethyl acetate, and dried in a vacuum desiccator. Yield of 4-(2'-hydroxyethoxy)-6-methoxy-m-phenylenediamine dihydrochloride is 7.2 g (69.2%).

EXAMPLES 6–9

3 milliliters of a solution of each of the following compositions

| SUBSTANCE | EXAMPLE NO. | | | |
|---|---|---|---|---|
| | 6 Wt % | 7 Wt % | 8 Wt % | 9 Wt % |
| p-Phenylenediamine | 0.2 | 0.08 | 0.2 | 0.08 |
| Resorcinol | — | 0.55 | — | 0.55 |
| m-Aminophenol | — | 0.04 | — | 0.03 |
| p-Aminophenol | — | 0.12 | — | 0.10 |
| 2-Methylresorcinol | — | 0.25 | — | 0.28 |
| 4-Chloro-6-(2'-hydroxyethoxy)-m-phenylenediamine dihydrochloride | 0.51 | 0.09 | — | — |
| 4,6-Bis-(2'-hydroxyethoxy)-m-phenylenediamine dihydrochloride | — | — | 0.56 | 0.09 |
| Sodium sulfite | 0.1 | 0.1 | 0.1 | 0.1 |
| Ethylenediamine tetraacetic acid (EDTA) | 0.02 | 0.02 | 0.02 | 0.02 |
| Erythorbic acid | 0.2 | 0.2 | 0.2 | 0.2 |
| Oleic acid | 12. | 12. | 12. | 12. |
| Propylene glycol | 18.8 | 18.8 | 18.8 | 18.8 |
| Isopropyl alcohol | 12.7 | 12.7 | 12.7 | 12.7 |
| Carbitol | 10. | 10. | 10. | 10. |
| Nonoxynol-4 (non-ionic ethoxylated surfactant) | 3.5 | 3.5 | 3.5 | 3.5 |
| Ammonium hydroxide | 8.0 | 8.0 | 8.0 | 8.0 |
| Fragrance | 0.3 | 0.3 | 0.3 | 0.3 |

-continued

| | EXAMPLE NO. | | | |
|---|---|---|---|---|
| SUBSTANCE | 6 Wt % | 7 Wt % | 8 Wt % | 9 Wt % |
| Deionized Water | to 100% | to 100% | to 100% | to 100% |
| Color result on gray hair | blue violet | light brown | blue violet | light brown | is mixed with 3 milliliters of 6% aqueous hydrogen peroxide and is applied to gray hair for approximately 20 minutes. The hair is dyed to the color indicated above.

COMPARATIVE EXAMPLE 1

3 milliliters of a solution of the following composition

| | |
|---|---|
| p-Phenylenediamine | 0.2 |
| 4,6-Dimethoxy-m-phenylenediamine | 0.443 |
| Sodium sulfite | 0.1 |
| EDTA | 0.02 |
| Sulfonated castor oil | 3. |
| Oleic acid | 12. |
| Propylene glycol | 12. |
| Sodium lauryl sulfate | 2. |
| Isopropyl alcohol | 21. |
| Ammonium hydroxide Conc. (28%) | 8. |
| Fragrance | 0.3 |
| Deionized water | to 100% | is mixed with 2 milliliters of 6% aqueous $H_2O_2$ and is applied to gray hair for approximately 20 minutes: the hair is found to be dyed blue.

However, after one washing with a mild shampoo, the intensity of the blue dye begins to fade severely, thus showing that the 4,6-dimethoxy-m-phenylenediamine coupler compound has unsatisfactory colorfastness.

In contrast, when each of the dyed hair samples in Examples 6-9 is similarly washed acceptable, color retention is observed even after many washing cycles.

EXAMPLES 10 and 11

| | Ex. 10 | Ex. 11 |
|---|---|---|
| p-Phenylenediamine | 0.2 | — |
| N,N—Bis(2-Hydroxyethyl)-p-phenylenediamine sulfate | — | 0.54 |
| 4-(2'-Hydroxyethyoxy)-6-methoxy-m-phenylenediamine dihydrochloride | 0.50 | 0.50 |
| Sodium sulfate | 0.1 | 0.1 |
| EDTA | 0.02 | 0.02 |
| Carbitol | 10. | 10. |
| Ethanol | 22. | 22. |
| Oleic acid | 12. | 12. |
| Ammonia | 8. | 8. |
| Ethylene glycol | 4.5 | 4.5 |
| Sodium lauryl sulfate | 1. | 1. |
| Hexylene glycol | 4. | 4. |
| Water | to 100% | to 100% |

When 3 milliliters of each of the above compositions is mixed with 3 milliliters of 4% hydrogen peroxide containing 1% hydroxyethyl-cellulose and is applied to the hair for approximately 10 to 30 minutes, a deeply colored dyed shade of blue is observed.

What is claimed is:

1. An oxidation dye coupler compound of the formula:

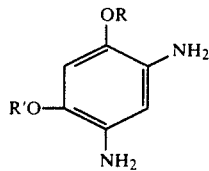

wherein each of R and R' independently represent mono or poly-hydroxy ($C_1$-$C_4$) alkyl or an acid addition salt thereof.

2. The compound of claim 1 wherein each of R and R' independently represent mono- or poly-hydroxy ($C_1$-$C_4$) alkyl.

3. The compound of claim 1 having the formula

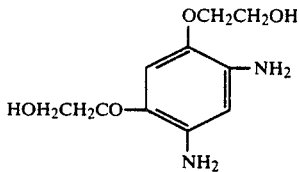

and the acid addition salts thereof.

4. A compound according to claim 1 having the formula

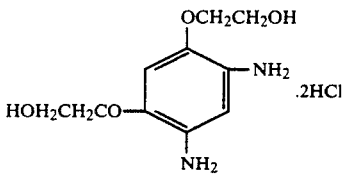

5. The compound of claim 1 having the formula

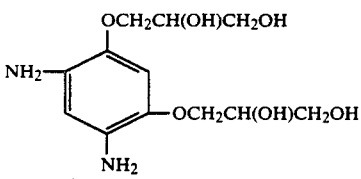

and the acid addition salts thereof.

6. A hair dyeing composition comprising an aqueous mixture of at least one oxidation dye coupler of the following formula:

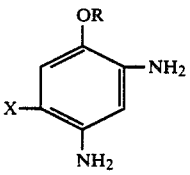

wherein R and R' are independently mono or polyhydroxy ($C_1$-$C_4$) alkyl or an acid addition salt thereof, and X represents the group —OR' where R' has the same meaning as R', the groups —OR and —OR' may be the same or different; and at least one oxidation base developer compound, said coupler and said developer being reactive with each other in the presence of an oxidizing agent to form a colored dye on hair.

7. The hair dyeing composition of claim 6, wherein said oxidation base developer compound is at least one paraphenylenediamine compound.

8. A hair dyeing composition according to claim 6 wherein at least one of R and R' is —CH$_2$CH$_2$OH.

9. A hair dyeing composition according to claim 6 wherein both R and R' are —CH$_2$CH$_2$OH.

10. A method for dyeing keratinic fibers which comprises applying to the fibers the hair dyeing composition of claim 6 in the presence of an oxidizing agent and allowing the mixture to remain in contact with the fibers for a period of time to effectively dye said fibers.

11. A method according to claim 6 comprising applying an oxidation dye coupler compound of the formula

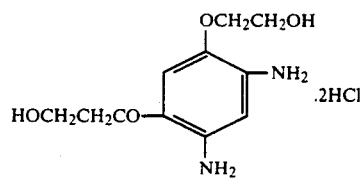

and a paraphenylenediamine developer compound, and the oxidizing agent comprises hydrogen peroxide.

12. The method of claim 11 wherein said keratinic fibers are human hair.

13. The method of claim 10 wherein said keratinic fibers are human hair.

14. A prepackaged unit dosage hair dyeing composition and oxidizing agent therefor, said package comprising in a first compartment a predetermined amount of the hair dyeing composition of claim 6 and in a second compartment a stabilized peroxide oxidizing agent in an amount sufficient to oxidize all of the oxidizable components of said hair dyeing composition in said first compartment, the contents of said first and second compartments being isolated from each other until just prior to use.

* * * * *

UNITED STATES PATENT AND TRADEMARK OFFICE
CERTIFICATE OF CORRECTION

PATENT NO. : 4,566,876
DATED : January 28, 1986
INVENTOR(S) : Keith C. Brown et al.

It is certified that error appears in the above-identified patent and that said Letters Patent are hereby corrected as shown below:

The formula in both claims 3 and 4 is correctly as follows:

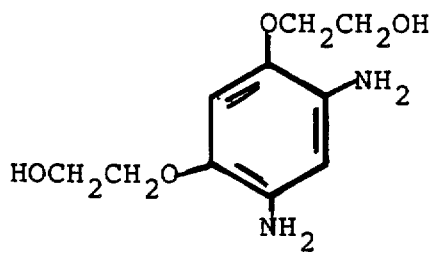

Signed and Sealed this

Sixth Day of October, 1987

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,566,876
DATED : January 28, 1986
INVENTOR(S) : Keith C. Brown et al.

It is certified that error appears in the above-identified patent and that said Letters Patent are hereby corrected as shown below:

The formula in claim 11 is correctly as follows:

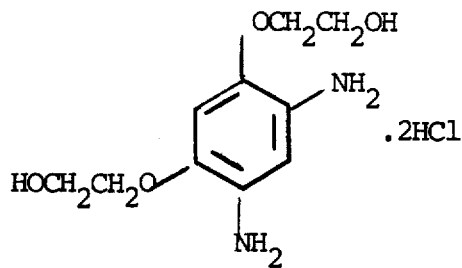

Signed and Sealed this

Twenty-ninth Day of December, 1987

*Attest:*

DONALD J. QUIGG

*Attesting Officer*         *Commissioner of Patents and Trademarks*